United States Patent [19]

Greenland et al.

[11] Patent Number: 4,467,921

[45] Date of Patent: Aug. 28, 1984

[54] VISUALLY CLEAR DENTIFRICE

[75] Inventors: Harry Greenland, West Ryde, Australia; Edward S. Hodgetts, North Brunswick, N.J.

[73] Assignee: Colgate-Palmolive Company, New York, N.Y.

[21] Appl. No.: 534,435

[22] Filed: Sep. 21, 1983

Related U.S. Application Data

[63] Continuation-in-part of Ser. No. 483,352, Apr. 8, 1983, abandoned.

[51] Int. Cl.$^3$ ................................................ A61K 7/16
[52] U.S. Cl. ........................ 206/524.4; 206/524.1; 424/49; 424/7.1
[58] Field of Search ...... 424/49–58; 206/524.1, 524.4

[56] References Cited

U.S. PATENT DOCUMENTS

| | | | |
|---|---|---|---|
| 3,309,274 | 3/1967 | Brilliant | 424/49 |
| 3,728,446 | 4/1973 | Roberts et al. | 424/49 |
| 3,903,252 | 9/1975 | Stearns et al. | 424/49 |
| 3,935,306 | 1/1976 | Roberts et al. | 424/49 |
| 4,064,229 | 12/1977 | Block et al. | 424/49 |
| 4,105,758 | 8/1978 | Schreiber | 424/49 |
| 4,141,969 | 2/1979 | Mitchell | 424/52 |
| 4,150,106 | 4/1979 | Assal et al. | 424/49 |
| 4,159,280 | 6/1979 | Wason | 424/52 |
| 4,223,003 | 9/1980 | Scheller | 424/49 |
| 4,302,439 | 11/1981 | Selwyn | 424/49 |
| 4,305,928 | 12/1981 | Harvey | 425/52 |
| 4,340,584 | 7/1982 | Wason | 424/52 |

FOREIGN PATENT DOCUMENTS 1289323 9/1972 United Kingdom .
2110083 6/1983 United Kingdom .

*Primary Examiner*—Shep K. Rose
*Attorney, Agent, or Firm*—Robert L. Stone; Murray M. Grill; Herbert S. Sylvester

[57] ABSTRACT

A visually clear dentifrice comprising sodium monofluorophosphate, an amorphous siliceous silica containing combined alumina polishing material and about 5–40 ppm of calcium ion to stabilize the dentifrice in an unlined aluminium tube. When a water-soluble dyestuff is present, the calcium ion stabilizes it against dye fading.

8 Claims, No Drawings

VISUALLY CLEAR DENTIFRICE

This application is a continuation-in-part of application Ser. No. 483,352, filed Apr. 8, 1983, now abandoned.

The present invention relates to visually clear dentifrices.

Visually clear dentifrices have been marketed in recent years in view of their desirable aesthetic aspect combined with their ability to provide desired hygenic and prophylactic effects to teeth and the oral cavity.

In visually clear dentifrices, it is necessary to select insoluble solid components with care since a close match between the refractive index of a solid component and the refractive index of the liquid vehicle is needed in order to provide clarity. For instance, a liquid vehicle mainly of glycerine and/or sorbitol with some water may be proportioned to have a refractive index of about 1.45 and a siliceous polishing material having a similar refractive index incorporated therein.

In order to increase their attractiveness, clear dentifrices may be dyed with water soluble dyes to make them red, yellow, orange, violet, blue, green or other colours. Indeed in British Pat. No. 1,289,323 a plurality of water-soluble dyes are used to make discreetly coloured portions of a clear dentifrice.

However, upon storage, dye colour often tends to fade.

Moreover, visually clear dentifrice containing both amorphous siliceous silica containing combined alumina polishing agent and a compound which provides fluorine tends to tarnish the inner surface of an unlined aluminium toothpaste tube.

It is an advantage of this invention that fluorine-providing visually clear dentifrice comprising silica containing combined alumina as polishing agent is stabilised for incorporation into an unlined aluminium tube.

It is a further advantage of this invention that dye colour of such visually clear dentifrice is stabilised.

Further advantages of the invention will be apparent from consideration of the following disclosure.

In accordance with certain of its aspects this invention relates to a visually clear dentifrice comprising about 0.05–7.6% by weight of sodium monofluorophosphate, about 20–80% by weight of a liquid vehicle wherein about 70–100% by weight of said liquid vehicle is humectant and the remainder is substantially water, said liquid vehicle having a refractive index between about 1.44 and about 1.47, about 0.02–10% by weight of gelling agent, about 5–50% by weight of an amorphous silica containing combined alumina polishing material having a refractive index similar to that of said liquid vehicle and a water soluble calcium salt in amount to provide about 5–40 ppm of calcium ion, said calcium ion serving to stabilise said visually clear dentifrice in an unlined aluminium tube.

In accordance with certain of its additional aspects this invention relates to a visually clear coloured dentifrice comprising about 0.05–7.6% by weight of sodium monofluorophosphate, about 20–80% by weight of a liquid vehicle wherein about 70–100% by weight of said liquid vehicle is humectant and the remainder is substantially water, said liquid vehicle having a refractive index between about 1.44 and about 1.47, about 0.02–10% by weight of gelling agent, about 5–50% by weight of an amorphous silica containing combined alumina polishing material having a refractive index similar to that of said liquid vehicle, about 0.1–1% by weight of a water soluble dyestuff, said amount being based on a solution of 1% by weight of said dyestuff in water, and a water soluble calcium salt in amount to provide about 5–40 ppm of calcium ion, said calcium ion serving to stabilise the colour of said dyestuff in said dentifrice and to stabilise said dentifrice in an unlined aluminium tube.

The problem of dye fading of visually clear coloured dentifrices was discussed in British Patent Application No. 81 35326 filed Nov. 24, 1981, corresponding to U.S. Ser. No. 444,099, filed Nov. 24, 1982, by Kenneth Harvey and Harry Hayes and assigned to Colgate-Palmolive Company. In that invention water-insoluble lakes were dispersed in the dentifrice. In the present invention, resort to such water-insoluble lake material need not be made in order to overcome dye fading.

In prior art U.S. Pat. Nos. 4,141,969 to Mitchell (Colgate-Palmolive Co.) and 4,159,280 to Wason (J. M. Huber, Corp.) and in his divisional U.S. Pat. Nos. 4,244,707 and 4,340,584, dentifrices are disclosed which contain amorphous siliceous polishing agent including silica containing combined alumina, and a compound which provides fluorine. Stability of these dentifrices, which typically contain substantial amounts of water, in unlined aluminium tube is provided by the presence of calcium, which may be added to the dentifrice in the form of a calcium salt. In the patent to Mitchell, it is taught that at least about 0.01 by weight (about 100 ppm) of calcium ion must be provided; in the patents to Wason, it is taught that at least about 0.005% by weight (about 50 ppm) of calcium ion must be present. Below these minimum levels tube incompatibilities occur. Dentifrices disclosed in these patents generally contain considerable amounts of water (over 35% by weight). Such dentifrices are inherently opaque and not visually clear.

In the patents to Wason, there is disclosure of adding 0.10% and 0.16% calcium to "Aim" clear-gel therapeutic toothpaste. Such commercial toothpaste did contain a lower water content than other toothpastes described in the patents. Based upon their experiments with higher water toothpaste, both patentees were dissuasive on using less than their indicated minimum calcium levels of calcium in order to provide tube compatibility.

In the present invention, tube stabilisation is achieved in visually clear dentifrice of low water content with low levels of calcium ion. As a further advantage, when dyestuff is present, dye fading is overcome.

The visually clear dentifrice of the present invention contains a liquid vehicle in amount of about 20–80% by weight. The humectants are selected and, with water if present, proportioned to provide the liquid vehicle with a refractive index between about 1.44 and 1.47. The most commonly employed humectants are glycerine (refractive index of 1.47 in 98% solution) and sorbitol (refractive index of 1.45 in 70% aqueous solution). Water separate of that which may be present in such humectant solutions may comprise up to about 5% by weight of the dentifrice. When water is present, it does not exceed about 30% of the liquid vehicle, including water present with humectant. Other humectants such as low molecular weight polyethylene glycols (e.g. having an average molecular weight of about 400–600) and propylene glycol may also be employed in a liquid vehicle having the proper refractive index. Water, when present separate from that in humectant solution, typically comprises about 1–5%, by weight of the liquid vehicle.

In addition to the liquid vehicle, the dentifrice contains a solid vehicle portion of a gelling agent, or a thickener to provide gel character to the dentifrice. Typical gelling agents are natural or synthetic gum or gumlike materials, e.g. Irish moss, gum tragacanth, alkali metal carboxymethyl or carboxyethyl cellulose, hydroxyethyl cellulose, xanthan, polyvinyl pyrrolidone, starch, water-soluble hydrophilic colloidal carboxyvinyl polymers such as those sold under the trade names Carbopol 934 and Carbopol 940 (CARBOPOL is a Trade Mark) and synthetic inorganic silicated clays such as those sold under the trade names Laponite CP and Laponite SP (LAPONITE is a Trade Mark). These grades of Laponite have the formula $$(Si_8Mg_{5.1}Li_{0.6}H_{7.6}O_{24})^-{}_{0.6}Na^+{}_{0.6}$$

The solid portion of the vehicle is typically present in an amount of about 0.02–10% by weight of the dentifrice preferably in the range of 0.5 to 5% by weight. When employed, grades of Laponite are preferably used in amounts in the range of from 1 to 5% by weight.

Synthetic finely divided silicas such as those sold under the trade names Cab-O-Sil M-5, Syloid 244, Syloid 266, Aerosil D200 and Zeosyl 200 and mixtures thereof may also be employed in amounts of from 0.02 to 10% by weight to promote thickening or gelling and to improve the clarity of the dentifrice.

The amorphous siliceous polishing agent may be essentially silica or may contain a small proportion (e.g. about 0.1 to 10%, typically about 1% by weight) of alumina which is combined with silica. Typical types of such amorphous siliceous polishing agents have been described in U.S. Pat. Nos. 3,911,102; 3,911,104; 3,906,090 each assigned to Colgate-Palmolive as well as in U.S. Pat. Nos. 3,893,340; 3,928,541; and 3,960,586, each assigned to J. M. Huber Corp.

In general sodium aluminosilicates (i.e. silica containing combined alumina) or silica xerogel having refractive indices in the range of about 1.44 to 1.47 are employed and the liquid vehicle is proportioned to have a refractive index similar to that of the polishing agent, typically within about 0.01 unit and preferably within about 0.005 unit or less. The polishing agent typically comprises about 5–50% by weight, preferably about 10–30% and most preferably about 15–25%, of the dentifrice.

The following list sets forth illustrative water-soluble dyestuffs which may be stabilised against dye fading in accordance with the present invention:

| WATER-SOLUBLE DYESTUFF | 1971 COLOUR INDEX NUMBER |
|---|---|
| FD & C Blue No. 1 | 42090 |
| D & C Red No. 33 | 17022 |
| Ponceau 4R (red) | 16255 |
| Carmoisine (red) | 14720 |
| Amaranth (red) | 16185 |
| Erythrosine (pink) | 45430 |
| Red 2 G (red) | 18050 |
| Green S (green) | 44090 |
| Indigo Carmine (blue) | 73015 |
| Patent Blue V (blue) | 42051 |
| Brilliant Blue FCF | 42090 |
| D & C Red No. 19 | 45170 |
| D & C Red No. 21 | 45380 |
| D & C Red No. 27 | 45410 |

Preferred dyestuff are D & C Red No. 33, FD & C Blue No. 1 L and Patent Blue V. Other dyestuffs, such as FD & C Yellow No. 6 may be mixed with additional dyestuff such as D & C Red No. 33 to adjust desired hue. Mixtures are desirably used. A 1% by weight water solution of the dyestuff is employed in the visually clear dentifrice in amount of about 0.1–1%, by weight, typically about 0.1–0.5% preferably about 0.2–0.3%.

Calcium is provided to the visually clear dentifrice in amount of about 5–40 ppm of calcium ion to stabilise the colour against dye fading. Water-soluble calcium salt such as calcium acetate, calcium nitrate or the soluble calcium halides (chloride; bromide; iodide) are used. Preferred amounts of calcium are about 5–10 ppm. It is noteworthy that such amounts do not stabilise the high water dentifrices of U.S. Pat. Nos. 4,141,969; 4,159,280; 4,244,707 and 4,340,584 in unlined aluminium tubes.

Fluorine-providing compound such as sodium monofluorophosphate, has a beneficial effect on the care and hygiene of the oral cavity, e.g. diminution of enamel solubility in acid and protection of the teeth against decay which do not substantially detract from the clarity of the dentifrice. Sodium monofluorophosphate suitably is present in an effective but non-toxic amount, within the range of about 0.05–7.6% by weight, preferably about 0.76–1.1%. Sodium monofluorophosphate may be mixed with sodium fluoride, in amount to provide about 0.01–1% by weight of total fluorine.

Organic surface-active agents may be used in the compositions of the present invention to achieve increased prophylactic action, assist in achieving thorough and complete dispersion of the compositions of the present invention throughout the oral cavity, and render the compositions of the present invention more cosmetically acceptable. The organic surface-active material may be anionic, nonionic, ampholytic, or cationic in nature, and it is preferred to employ as the surface-active agent a detersive material which imparts to the composition detersive and foaming properties. Suitable types of such detergents include water-soluble salts of higher fatty acid monoglyceride monosulphates, such as the sodium salt of the monosulphated monoglyceride of hydrogenated coconut oil fatty higher alkyl sulphates, such as sodium lauryl sulphates, sodium $C_{12-18}$ alkyl sulphate, alkyl aryl sulphonates, such as sodium dodecyl benzene sulphonate, olefin sulphonates, such as sodium olefin sulphonate in which the olefin group contains 12–21 carbon atoms, higher alkyl sulphoacetates, higher fatty acid esters of 1,2-dihydroxy propane sulphonates, and the substantially saturated higher aliphatic acyl amides of lower aliphatic amino carboxylic acid compounds, such as those having 12–16 carbons in the fatty acid alkyl or acyl radicals. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosine compounds in dentifrice compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Other particularly suitable surface-active materials include nonionic agents such as condensates of sorbitan monostearate with approximately 20 moles of ethylene oxide, condensates of ethylene oxide with propylene oxide, "Pluronic" materials and amphoteric agents as long chain (alkyl) amido-alkylene-alkylated amine derivatives, which are available under the trademark "Miranol" C₂M. Cationic surface active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12-18 carbon atoms) and two (poly) oxyethylene groups attached to the nitrogen (typically containing a total of from about 2 to 50 ethanoxy groups per molecule) and salts thereof with acids, and compounds of the structure:

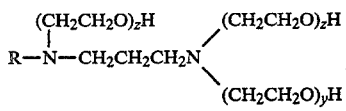

where R represents a fatty alkyl group containing from about 12 to 18 carbon atoms, and x, y and z total 3 or higher, as well as salts thereof with mineral or organic acids, may also be used. It is preferred to use from about 0.05 to 5% by weight of the foregoing surface-active materials in the dentifrice of the present invention.

Any suitable flavouring or sweetening materials may be employed in formulating a flavour for the compositions of the present invention. Examples of suitable flavouring constituents include the flavouring oils, e.g. oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cylamate, perillartine and saccharine. Suitably, flavour and sweetening agents may together comprise from about 0.01 to 5% or more of the composition of the present invention. Chloroform may also be used.

Various other materials may be incorporated in the oral preparations of this invention. Examples thereof are preservatives, silicones, chlorophyll compounds, ammoniated materials such as urea, diammoniumphosphate and mixtures thereof and other constituents. The adjuvants are incorporated in the compositions of the present invention in amounts which do not substantially adversely affect the properties and characteristic desired and are selected and used in proper amounts depending upon the particular type of preparation involved.

Antibacterial agents may also be employed in the oral preparations of the present invention in an amount of about 0.01-5% by weight. Typical antibacterial agents include:
N¹-(4-chlorobenzyl-N⁵-(2,4-dichlorobenzyl biguanide);
p-chlorophenyl biguanide;
4-chlorobenzhydryl biguanide;
4-chlorobenzhydrylguanylurea;
N-3-lauroxypropyl-N⁵-p-chlorobenzylbiguanide;
1,6-di-p-chlorophenylbiguanidohexane;
1,6-bis(2-ethylhexylbiguanido) hexane;
1-(lauryldimethylammonium)-8-(p-chlorobenzyldimethylammonium) octane dichloride;
5,6-dichloro-2-guanidinobenzimidazole;
N¹-p-chlorophenyl-N⁵-laurylbiguanide;
5-amino-1,3-bis(2-ethylhexyl)-5-methylhexahydro pyrimidine;
and their non-toxic acid addition salts.

In the manufacture of dentifrices, it is conventional to remove entrained air from the product by deaeration under vacuum typically at a late stage in the manufacture. If desired the dispersed, immobile air bubbles desirably can be permitted to remain as they can enhance the appearance of the dentifrice. Furthermore, air can be at least partially removed and reintroduced as substantially globular or spheroidal bubbles of say about 0.1-8 mm, preferably about 0.5-5 mm in size, well distributed in the gel at an average of at least one per cubic centimeter. Such air bubbles may be placed in the gel by stirring it while introducing air. Instead of air, bubbles of another gas, such as nitrogen or carbon dioxide, can be introduced in non-toxic quantity. In particular, carbon dioxide can provide an effervescent character to the dentifrice.

In the event it is desired to have a minimum amount of air in the dentifrice of the present invention, the "Unimix" apparatus described in "Process Engineering" Sept. 11, 1970, pages 81-85, is particularly efficacious for this purpose. In this apparatus a mixing tool can be rotated in clockwise or counterclockwise manner, and the action of the mixing tool is followed by the action of a scraper blade to ensure that the working surface of the apparatus is scraped clean.

Preferably, a plastic such as polytetrafluorethylene is used as the scraper blade since it is compatible with the various ingredients of the dentifrice. The positioning of the mixing tool and the scraper from a raised central column in the apparatus and the further presence of a hydraulically operated vacuum-tight lid permits but little air to enter the formulation during processing. Thus, gelling agent and a portion of liquid including water and/or humectant can be efficiently blended in the Unimix apparatus. Then the remaining liquid can be separately blended with the polishing agent and additional components (except for post-added components, such as flavouring oil) in the Unimix, and then the two dispersions blended together in the Unimix apparatus. If desired, the small amount of air can be largely removed under the depressurized conditions in the apparatus. The apparatus can be used to blend ingredients at room temperature as well as at higher temperatures.

Furthermore, if desired, visible particles of dyes, pearlescent flakes or particles of insoluble salts of antibacterial agents such as the monofluorophosphate salt or the disarcosinate salt of 1,6-di-p-chlorophenylbeguanidohexane, as well as other particles, can be distributed in the dentifrice.

The dentifrices should have a pH practicable for use. A slightly acid to slightly alkaline pH is preferred. The dentifrices may be packaged in lined or unlined aluminium tubes, lined lead tubes, plastic tubes or aerosel or pump tubes.

The invention may be put into practice in various ways and specific embodiments will be described to illustrate the invention with reference to the accompanying example. All amounts are by weight unless otherwise indicated.

EXAMPLE

The following visually clear dentifrices are prepared and placed in an unlined aluminium tube:

|  | PARTS | |
| --- | --- | --- |
|  | A | B |
| Glycerine (98%) | 26.5000 | 26.5000 |
| Sorbitol (70%) | 39.4626 | 39.4600 |
| Polyethylene glycol 600 | 3.0000 | 3.0000 |
| Water | 3.0000 | 3.0000 |
| Sodium saccharin | 0.1800 | 0.1800 |
| Sodium monofluorophosphate | 0.7600 | 0.7600 |
| Sodium alumino silicate-amorphous (silica containing about 1%, combined alumina-Zeo 49) | 17.0000 | 17.0000 |
| Silica aerogel (Syloid 244) | 5.7000 | 5.7000 |
| Colour | | |
| D & C Red No. 33 (1%) | 0.3000 | 0.3000 |
| FD & C Yellow No. 6 (1%) | 0.4000 | 0.4000 |
| Sodium lauryl sulphate | 2.0000 | 2.0000 |
| Flavour | 1.1000 | 1.1000 |
| Calcium acetate monohydrate | — | 0.0026 |

Visually clear dentifrice B contains 6 ppm of calcium ion.

Both visually clear dentifrices are initially bright red in colour. However, after aging for 13 weeks at 43° C., the colour of Dentifrice A fades, while the colour of Dentifrice B remains bright after aging for 13 weeks at 43° C.

Tarnishing occurs on the inner surface of the aluminium tube containing Dentifrice A after aging for 9 weeks at 49° C., while the inner surface of the aluminium tube containing Dentifrice B remains bright after aging for 9 weeks at 49° C.

Colour fading and tube tarnishing are also prevented when Dentifrice B is modified to contain 0.0176 parts of calcium acetate (40 ppm of calcium ion) and 0.0022 parts of calcium acetate (5 ppm of calcium ion).

When opaque dentifrice is prepared containing 25 parts of glycerine, 0.5 parts of sodium benzoate, 0.2 parts of sodium saccharin, 1.1 parts of sodium carboxymethyl cellulose, 30 parts of amorphous Zeo 49, 0.5 parts of calcined alumina, 1.0 part of alpha-alumina trihydrate, 0.5 parts of titanium dioxide, 1.5 parts of sodium lauryl sulphate, 1 part of flavour, colour containing D & C Red No. 33 (1%)—0.3 parts and FD & C Yellow No. 6 (1%)—0.4 parts and water in amount to total 100 parts, and placed in an unlined aluminium tube, after aging for 6 weeks at 43° C., the initially bright colour fades and the inner tube surface is tarnished and gas formation occurs.

When the opaque dentifrice is modified by addition of 0.0026 parts of calcium acetate (6 ppm of calcium ion), after aging for 6 weeks at 43° C. there is dye fading, tube tarnishing and gas formation.

When the opaque dentifrice is modified by addition of 0.0176 parts of calcium acetate (40 ppm of calcium ion), there is dye fading and tube tarnishing.

Although this invention has been illustrated with reference to specific formulations, it will be apparent to one skilled in the art that various modifications may be made thereto which fall within its scope.

We claim:

1. A visually clear dentifrice contained in an unlined aluminium tube, said dentifrice comprising about 0.05–7.6% by weight of sodium monofluorophosphate, about 20–80% by weight of a liquid vehicle wherein about 70–100% by weight of said liquid vehicle is humectant and the remainder is substantially water, said liquid vehicle having a refractive index between about 1.44 and 1.47, about 0.02–10% by weight of gelling agent, about 5–50% by weight of an amorphous silica containing combined alumina polishing material having a refractive index similar to that of said liquid vehicle and a water soluble calcium salt in amount to provide about 5–40 ppm of calcium ion, said calcium ion serving to stabilise said visually clear dentifrice in an unlined aluminium tube.

2. The visually clear dentifrice claimed in claim 1 wherein said polishing agent is silica containing about 0.1–10% by weight of combined alumina.

3. The visually clear dentifrice claimed in claim 2 wherein said amorphous siliceous polishing agent is silica containing 0.1–1% by weight of combined alumina.

4. The visually clear dentifrice claimed in claim 1 wherein said water soluble calcium salt is present in amount to provide about 6 ppm of calcium ion.

5. The visually clear dentifrice claimed in claim 1 wherein said water soluble calcium salt is calcium acetate.

6. The visually clear dentifrice claimed in claim 1 wherein there is present about 0.1–1% by weight of a water-soluble dyestuff, said amount being based on solution of 1% by weight of said dyestuff in water, said dyestuff initially providing colour to said dentifrice but undergoing colour fading during aging of said dentifrice in the absence of said calcium ion, said calcium ion serving to stabilise the colour of said dyestuff in said dentifrice.

7. The visually clear dentifrice claimed in claim 1 wherein said water soluble calcium salt is present in amount to provide about 6 ppm of calcium ion.

8. The visually clear dentifrice claimed in claim 6 wherein said water soluble calcium salt is calcium acetate.

* * * * *